United States Patent
Honda et al.

(10) Patent No.: US 7,432,503 B2
(45) Date of Patent: Oct. 7, 2008

(54) SCANNING ELECTRON MICROSCOPE AND METHOD FOR DETECTING AN IMAGE USING THE SAME

(75) Inventors: Toshifumi Honda, Yokohama (JP); Hiroshi Makino, Kokubunji (JP)

(73) Assignee: Hitachi High-Technologies Corporation, Tokyo (JP)

(*) Notice: Subject to any disclaimer, the term of this patent is extended or adjusted under 35 U.S.C. 154(b) by 215 days.

(21) Appl. No.: 11/319,721

(22) Filed: Dec. 29, 2005

(65) Prior Publication Data

US 2006/0151700 A1  Jul. 13, 2006

(30) Foreign Application Priority Data

Jan. 13, 2005 (JP) ............... 2005-005882

(51) Int. Cl.
G01N 23/00 (2006.01)

(52) U.S. Cl. ............... 250/310; 250/306; 250/307; 250/311; 250/442.11

(58) Field of Classification Search ............... 250/310, 250/306–443.1
See application file for complete search history.

(56) References Cited

U.S. PATENT DOCUMENTS

| 4,864,131 | A | * | 9/1989 | Rich et al. ............... 250/308 |
|---|---|---|---|---|
| 4,933,565 | A | * | 6/1990 | Yamaguchi et al. ....... 250/492.2 |
| 5,063,293 | A | * | 11/1991 | Rich et al. ............... 250/308 |
| 6,476,389 | B1 | * | 11/2002 | Konakawa et al. ........ 250/310 |
| 6,992,287 | B2 | * | 1/2006 | Sullivan ................... 250/306 |
| 2002/0142496 | A1 | * | 10/2002 | Nakasuji et al. ........... 438/14 |
| 2003/0205678 | A1 | * | 11/2003 | Notte ................... 250/423 F |
| 2004/0075051 | A1 | * | 4/2004 | Sullivan ................... 250/307 |
| 2005/0098724 | A1 | * | 5/2005 | Sullivan ................... 250/310 |

FOREIGN PATENT DOCUMENTS

JP  2003-016983  1/2003

\* cited by examiner

*Primary Examiner*—Jack I. Berman
*Assistant Examiner*—Andrew Smyth
(74) *Attorney, Agent, or Firm*—Antonelli, Terry, Stout & Kraus, LLP.

(57) ABSTRACT

In the present invention, in order to realize both a reduction of an image detecting time and high quality image detection in a scanning electron microscope for measurement, inspection, defect review, or the like of semiconductor wafers, a low-magnification image is taken by using a large beam current; a high-magnification image is taken by using a small beam current; control amounts for correcting a change in luminance, a focus deviation, misalignment, and visual field misalignment of taken images, which are generated due to a variation of a beam current are saved in advance in a memory of an overall control system; and these amounts are corrected every time the beam current is switched, thereby making it possible to take the images without any adjustment operation after switching the currents.

11 Claims, 8 Drawing Sheets

Low Magnification

High Magnification

SCANNING ELECTRON MICROSCOPE AND METHOD FOR DETECTING AN IMAGE USING THE SAME

CROSS-REFERENCE TO RELATED APPLICATION

The present application claims priority from Japanese patent application No. JP 2005-005882 filed on Jan. 13, 2005, the content of which is hereby incorporated by reference into this application.

BACKGROUND OF THE INVENTION

The present invention relates to a scanning electron microscope (hereinafter, referred to as "SEM: Scanning Electron Microscope") and an image detecting method thereof for detecting an image of a surface of an observation target by irradiating a convergent electron beam to the observation target such as a semiconductor wafer and detecting electrons emitted from the irradiated position, and particularly relates to a technique effectively applied to an SEM semiconductor wafer inspection apparatus required to take high-magnification images, a review SEM for observing in greater detail defects detected in the semiconductor wafer, and a length measurement SEM for measuring a pattern formed on the semiconductor wafer, etc.

As a technique that the present inventors have studied, the following techniques are conceivable in, for example, the SEM semiconductor wafer inspection apparatus, and the review SEM, the length measurement SEM, etc. (for example, see Japanese Patent Laid-Open Publication No. 2003-16983).

Along with miniaturization of the patterns on the semiconductor wafer, control of a front-end manufacture process of semiconductor is becoming more and more difficult; detection of defect, observation, and dimension measurement of pattern width in the optical microscope are becoming difficult; and inspection, review (reexamination), and length measurement are performed based on the images taken by the SEM.

The SEM emits an electron beam converged on a surface of the observation target, and detects a secondary electron or reflected electron emitted from the irradiated position. When the irradiated position of the electron beam is two-dimensionally moved, a two-dimensional image is taken.

Expected values of the secondary electron and the reflected electrons then emitted upon irradiation of the electron beam are known to be proportional to a beam current which controls an amount of electron beams to be irradiated. The number of the emitted secondary electrons is not completely the same in the case of the same beam current, a variation occurs in the emitted number, and the variation is proportional to the emitted electron number to one-half power. This variation is generally known to be a main factor of noise of the detected image in SEM.

Regarding an S/N of detected images, the symbol "S" indicating a signal is proportional to the beam current and the variation which is a noise component is proportional to the beam current to one-half power, so that the S/N is proportional to the beam current to the one-half power. It is known that, for this characteristic, in order to obtain the image with the good S/N, the image has to be detected by use of the beam current which is as large as possible.

However, it is known that, when the beam current is increased, aberration of an electro-optical system is increased and a beam diameter is increased. Therefore, there has been a problem that high-resolution images cannot be obtained. As a technique for solving this problem, a noise reduction technique which is performed by addition through a frame is known. This is a method in which a plurality of images within the same region are taken and each of the images is used as a frame and the frames are integrated to synthesize a final image. When this method is employed, the S/N is proportional to the number of added frames to the one-half power, while the image taken time increases in proportion to the number of added frames.

By the SEM having such a characteristic, defects of the semiconductor are reviewed or the dimensions of the semiconductor pattern are measured. However, when such processes are to be performed, two types of images are generally taken, i.e., low-magnification image detection and high-magnification image detection are performed. For example, in the review SEM for reviewing the defects of semiconductor, the defect is enlarged at high magnification and displayed in accordance with defect coordinates outputted by an inspection device for detecting the defects. However, accuracy of the defect coordinates outputted by the inspection device is bad within a visual field of the high-magnification image. Therefore, first, a defect position is specified by comparing the low-magnification defect image with a reference image which is a normal image having the same pattern as that of the defect image, and the defect position is enlarged to obtain the high-magnification image.

On the other hand, in the length measurement SEM, in order to determine a pattern to be measured, a low-magnification image is similarly detected. The image is taken subsequently at high magnification in order to perform measurement with high accuracy, and line width etc. is measured from the taken image.

SUMMARY OF THE INVENTION

Incidentally, the present inventors have studied the technique of the SEM as described above and, as a result, the following has been apparent.

That is, in the above-described conventional techniques, the beam current at the low-magnification image detection and the beam current at the high-magnification image detection have to be the same. Therefore, there has been a problem that when a magnification difference between the high-magnification image and the low-magnification image is large, an image taken time of the low-magnification image becomes longer.

Hereinafter, an example of the review SEM will be described. Although the low-magnification image is used as an image employed for detecting the defects. However, since defect-detection coordinate accuracy of the inspection device with respect to size of the defect is bad, the high-resolution image has to be taken in a large visual field. Even if a pitch of semiconductor pattern is reduced to 65 nm in the future, the size of defect which has to be detected within the visual field thereof is conceived to be about 25 nm, which is sufficiently large when compared with the resolution of a general SEM, for example, with 4 nm.

Meanwhile, the defect-detection coordinate accuracy in the inspection device is particularly bad in a dark-field inspection device, for example about ±4 µm in accuracy. For this reason, a defect with about 25 nm is required to be detected from an 8-µm square visual field. However, when the image is taken by sampling the visual field by 512×512, the defect is detected in about 1.5 pixels, so that a high defect capturing rate cannot be expected. In order to improve the defect capturing rate, a method of, for example, doubling a density of sampling is required. However, in this case, taking the image by the same S/N requires a time that is four times longer.

On the other hand, when the sampling is performed with a doubled density, i.e., at 1024×1024, the size per pixel becomes about 8 nm which is twice or more of the resolution of the SEM having been described above as an example. Therefore, even when a beam spot diameter is somewhat increased by increasing the beam current, the image can be taken without deteriorating the resolution in the taken image.

However, there is a problem that, when the same beam current is used for taking the high-magnification image, the image of higher resolution cannot be obtained. For example, when the defect of about 25 nm is to be taken in a size of about one eighth of the image, the image detection in a 200-nm square visual field is required. When this is sampled by 512× 512, the size per pixel becomes about 0.4 nm. This is a resolution that the general SEM cannot reach and, moreover, in a state in which the beam current is large, the resolving power is apparently insufficient.

Thereat, although a method of setting an optimum beam current for each of the low-magnification image and the high-magnification image is conceivable, the conventional method has been incapable of setting the above optimum beam current.

A reason for that includes a first problem of an occurrence of misalignment of visual fields after being shifted between the small beam current and the large beam current and misalignment of the beam. In the high-resolution SEM, generally, a FE (field-emission) electron gun or a schottky emission electron gun is employed as an electron source. In order to change the beam current by the FE electron gun, the extraction voltage of the FE electron gun is changed. When the extraction voltage is changed herein, an assumed light source position is changed, whereby the visual field misalignment and misalignment in the axis of the electron gun occurs. Therefore, in order to take the good image in an axis-adjusted state, adjusting the alignment of the axis has been required every time the beam current is changed.

A second problem is a switching time of the current. When shortening an image taken time of the low-magnification image is considered to be a main purpose of beam current switching, the switching of the current has to be carried out at an at least shorter time than the image taken time of the low-magnification image. Generally, the image taken time of the SEM is about 640 ms in terms of 16 frame additions in an image sampling of 512×512. In order to ensure the same S/N in a sampling of 1024×1024, four times the image taken time of the SEM, i.e., 2560 ms is required. Herein, when two images, i.e., a defect image and a reference image which it is known that previously has the same pattern as that of the defect image are taken at the low magnification, it takes 5120 ms. A shortened time in the case where the beam current is increased four times and the low-magnification defect image and reference image are taken 1280 ms becomes 3840 ms, so that the beam current has to be switched within an at least shorter time than 3840 ms.

However, when the extraction voltage of the FE electron gun is changed, a period of time is generally consumed more than until the beam current is stabilized and the overall image taken time has not been shortened even when the beam current is switched.

Moreover, the beam current can be changed by controlling a suppressor voltage in the case of using the schottky emission electron gun. Also in this case, however, similarly to the case where the extraction voltage of the FE electron gun is changed, there is a problem that a period of time is consumed until it is stabilized.

An object of the present invention is to realize both shortening of the image taken time and obtaining of the high-quality image detection in the SEM.

The above and other objects and novel feature of the present invention will become apparent from the description of the present specification and the accompanying drawings.

Outlines of representative ones of inventions disclosed in the present application will be briefly described as follows.

More specifically, an SEM according to the present invention has: a control amount memory means for saving, in advance, an adjustment amount of a gain adjusting means for making a detection value of an electron detector falling within a predetermined range in setting a plurality of beam currents, or a calculation algorithm of the adjustment amount; and an image detecting condition control means for changing an image detecting condition in accordance with a change of the beam current by using the adjustment amount or calculation algorithm of the adjustment amount saved in the control amount memory means.

In addition, an image detecting method of an SEM according to the present invention includes a first image detecting step of making an electron beam converged into a spot-like shape being scanned on an observation target surface, and converting a secondary electron or reflected electron generated in the scan into an electrical signal so as to form an image; a defect position specifying step of specifying a defect position on the observation target surface based on the image formed in the first image detecting step; a second image detecting step of making an electron beam converged into a spot-like shape being scanned at a defect position specified in the defect position specifying step by using a magnification larger than the magnification in the first image detecting step, and converting a secondary electron or reflected electron generated in the scan into an electrical signal so as to form an image; a first beam current changing step of observing the observation target surface in the second image detecting step by using a beam current smaller than a beam current of the first image detecting step; a first image detecting condition setting step of changing an image detecting condition to a condition set in advance for detecting an image by using the beam current set in the first beam current changing step; a second beam current changing step of setting the beam current employed in the first image detecting step; and a second image detecting condition setting step of setting the image detecting condition employed in the first image detecting step again, wherein the first beam current changing step and the first image detecting condition setting step are performed before the second image detecting step and the second beam current changing step and the second image detecting condition setting step are performed after the second image detecting step.

According to the SEM and the image detecting method according to the present invention, the electron beam can be switched within a short period of time, and both the short-time low-magnification image detection and the high-resolution high-magnification image detection can be performed.

These and other objects, features and advantages of the invention will be apparent from the following more particular description of preferred embodiments of the invention, as illustrated in the accompanying drawings.

DESCRIPTION OF THE PREFERRED EMBODIMENTS

Figure 1:
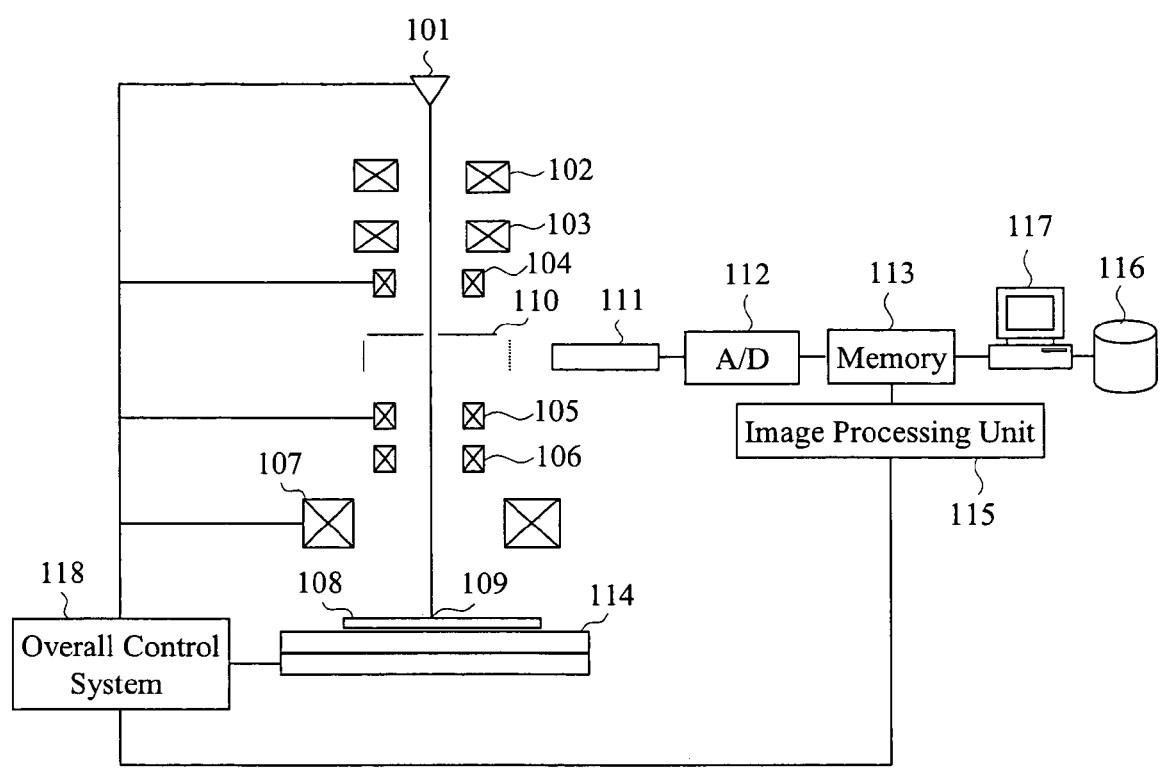
FIG. 1 is a view showing a configuration of an SEM according to an embodiment of the present invention.

Hereinafter, embodiments of the present invention will be detailed based on the drawings. Note that, throughout all the drawings for explaining the embodiments, the same members are denoted in principle by the same reference numeral and the repetitive description thereof will be omitted.

In a semiconductor wafer, patterns are formed in a multi-layered structure through many steps. In order to monitor a manufacture process in a flow of producing the multi-layered structure, a dimensional measurement of a pattern formed per layer, a visual inspection of the patter, and a review (reexamination) of a defect detected in the visual inspection have been performed.

A recent semiconductor process is increasingly made fine. Therefore, a SEM capable of take an image with resolution higher than that of an optical microscope has been applied as an image detection for performing the process. A review SEM has been widely used as the SEM employed for such a purpose. A main function of the review SEM is to move a visual field to a defect position in accordance with the coordinates of the defect which has been detected in the visual inspection and to take an image of the defect by the SEM.

FIG. 1 is a view showing a configuration of an SEM according to an embodiment of the present invention. First, an example of the configuration of the SEM according to the present embodiment will be described with reference to FIG. 1.

The SEM of the present embodiment is, for example, a review SEM and is comprised of an electron beam source 101, condenser lenses 102 and 103, an electron beam axis adjuster 104, scanning units 105 and 106, an objective lens 107, an E×B (E cross B) 110, an electron detector 111, an A/D converter 112, a memory 113, an XY stage 114, an image processing unit 115, a secondary storage device 116, a computer terminal device 117, and an overall control system 118, etc.

An operation of the SEM according to the present embodiment will next be described with reference to FIG. 1.

The electron beam source 101 emits an electron beam. The emitted electron beam passes through the condenser lenses 102 and 103, and then astigmatism and misalignment are corrected by the electron beam axis adjuster 104. The electron beam is deflected by the scanning units 105 and 106 so as to control a position where the electron beam is irradiated. Then, the electron beam is converged by the objective lens 107 to irradiate an image detecting target 109 of a wafer 108. As a result, a secondary electron and a reflected electron are emitted from the image detecting target 109, and the secondary electron and reflected electron are deflected by the E×B 110 and detected by the electron detector 111. The secondary electron and reflected electron detected by the electron detector 111 are converted into digital signals by the A/D converter 112 and stored in the memory 113. An XY stage 114 moves the wafer 108, thereby making it possible to take images at some positions of the wafer 108. The image processing unit 115 detects a defect position based on the image stored in the memory 113. A detection method thereof includes a method in which the image at the defect position is compared with an image at a reference position, which it is expected that has the same pattern as that of the image of the defect position, and which detects as a defect a position where a difference between both images exists. The secondary storage device 116 can store the image stored in the memory 113. The computer terminal device 117 can display the image stored in the secondary storage device 116 or the memory 113. Also, the user can carry out setting of various operations of the terminal device by performing an input to the computer terminal device 117. The overall control system 118 controls axis adjustment of the electron beam, deflection of the electron beam performed by the scanning units 105 and 106, and visual field transfer by movement of the XY stage 114.

Figure 2:
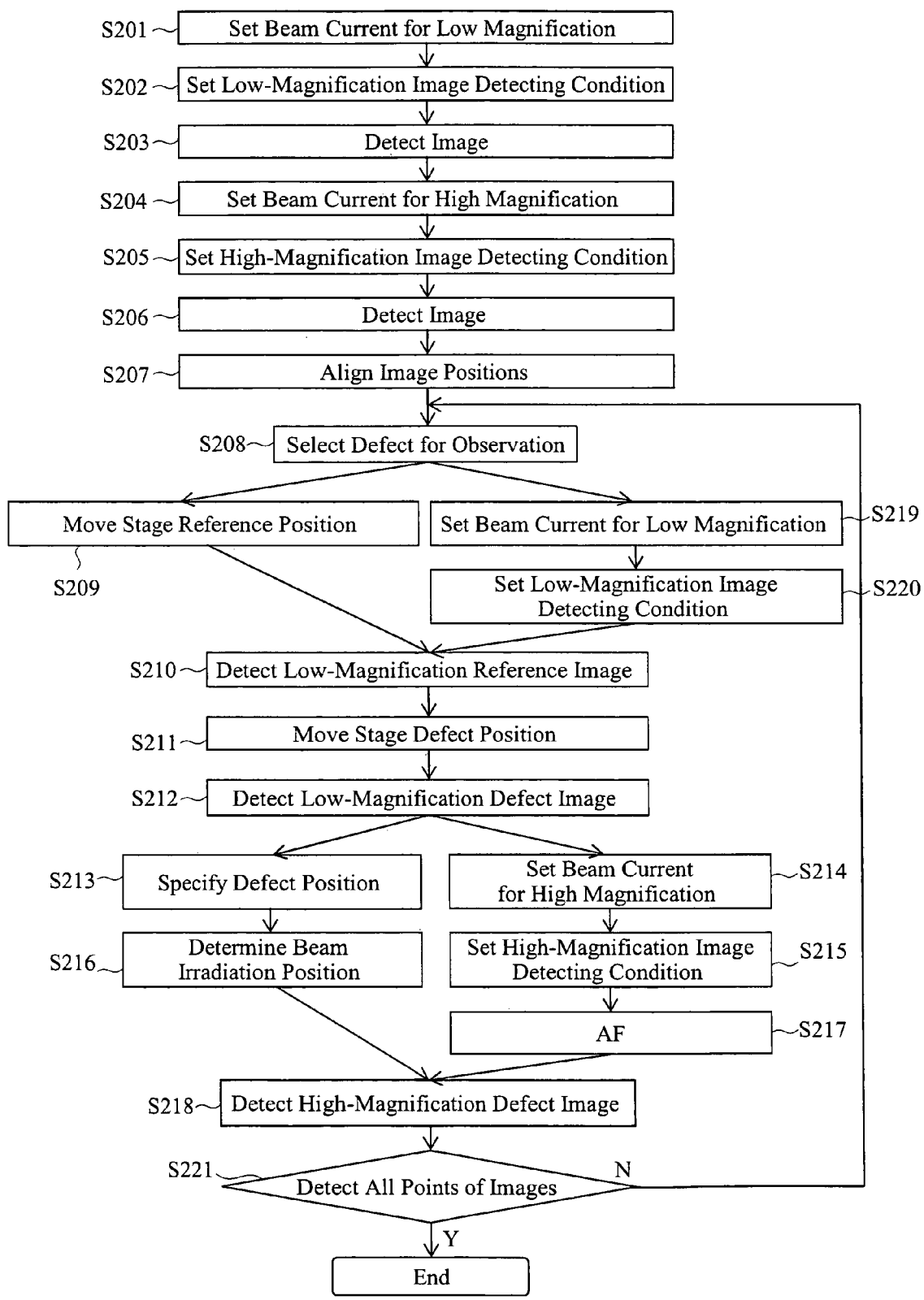
FIG. 2 is a flow chart showing a sequence of the case where defect images are automatically taken in the SEM according to the first embodiment of the present invention.

A sequence of taking an image defect by the SEM according to the present embodiment will next be described with reference to FIG. 2. FIG. 2 is a flow chart showing a sequence of taking the defect image in the SEM shown in FIG. 1. The following operations are basically automatically performed in accordance with control executed by, for example, the overall control system 118, wherein its portion can be manually executed via, for example, the computer terminal device 117.

First, a beam current for taking a low-magnification image is set in step S201. Then, in step S202, alignment of the axis is adjusted for the current, astigmatism is corrected, and a control value for performing this correction is saved in a memory in the overall control system 118. The correction may be performed manually, or a method disclosed in Japanese Patent Laid-Open Publication No. 2003-16983 may be employed.

Then, an image is taken in step S203. Next, a beam current for taking a high-magnification image is set in step S204, the axis at the beam current for taking the high-magnification image is aligned in step S205, astigmatism is corrected, and a control amount for performing this correction is saved in the memory in the overall control system 118.

In step S206, an image is taken by the beam current for taking a high-magnification image. In step S207, the position of the image taken in step S203 and that of the image taken in step S206 are aligned, and a position misalignment amount is saved in the memory in the overall control system 118.

In step S208, a defect to take an image is selected. In step S209, the XY stage 114 is moved, whereby a reference position corresponding to the selected defect enters the visual field of the SEM. At the same time, the beam current is switched in step S219 (second beam current changing step), and setting of the electro-optical system for taking the low-magnification image is performed in step S220 (second image detecting condition setting step). More specifically, a normal control amount of the electro-optical system for taking the low-magnification image is set, and concurrently the alignment of the axis of the beam current for taking the low-magnification image and the control amount for astigmatism correction, which have been saved in step S202, are set.

In step S210, a reference image is taken. In step S211, the XY stage 114 is moved so that the defect selected in step S208 enters the visual field of the SEM.

The image is taken in step S212 (first image detecting step), and a position of the defect is specified in step S213 (defect position specifying step) by comparing the image taken in step S210 and the image taken in step S212 in step S213 (defect position specifying step). At the same time, the beam current is varied for high-magnification image in step S214 (first beam current changing step), and setting of the electro-optical system for taking the high-magnification image is performed in step S215 (first image detecting condition setting step). More specifically, a normal control amount of the electro-optical system for taking the high-magnification image is set, and the alignment of the axis of the beam current for taking the high-magnification image and the control amount for the astigmatism correction, which have been saved in step S205, are set.

In addition, in step S216, based on misalignment amounts of the low-magnification image detection and the high-magnification image detection measured in step S207, an electron beam irradiating position where the defect is taken at a center of the visual field is calculated when the electron beam is emitted.

In step S217, an AF (automatic focus) is performed. In step S218 (second image detection), the high-magnification image is taken. This image is stored in the memory 113 or the secondary storage device 116.

In step S221, it is checked whether all points of the image are taken. If images of all the points have been taken, the process is ended. If the images of all the points have not been taken, the process returns to step S208 and the steps S208 to S221 are executed again.

By using the above-described method, the low-magnification images and high-magnification images can be taken without being affected by the misalignment or astigmatism variation caused when the beam current is changed.

Also, when the beam current of the electron beam source 101 is changed, the position where the electron beam is focused is changed depending on a configuration of the electro-optical system in some cases. Therefore, handling of such cases may be carried out by: performing the AF in step S202 and step S205; serving the control amount in which the focuses of the respective beam currents coincide with one another; and being corrected by the saved control amount so that the focuses in step S220 or step S215 coincide with each other.

Generally, the electron detector 111 comprises a combination of a scintillator and a photomultiplier in many cases. When the beam current is varied for the low-magnification images and high-magnification images, the number of detected electrons varies, so that adjustment of a gain of the photomultiplier is required. Therefore, the gain of the photomultiplier which enables the respective beam currents to take the good images may be obtained in step S202 and step S205 and, at the same time, the gains suitable for the respective beam currents in step S215 and step S220 may be set.

It should be noted that saving previously the control amounts suitable for the respective beam currents has been described, an expression for calculating values of the control amounts may be saved so as to set the control amounts in step S220 and S215 based on the expression. For example, as for the gain of the photomultiplier, since it is understood in advance that the beam current is approximately proportional to the number of secondary electrons and reflected electrons generated by the current, a method of making the gain of the photomultiplier inversely proportional to the beam current may be used.

Figure 9:
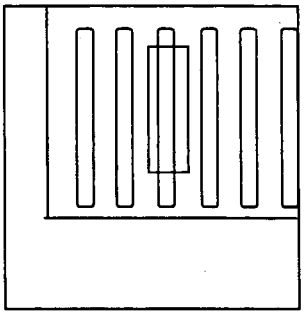
FIG. 9 is a view showing an example of a GUI for inputting image taken conditions in a sequence of a defect image detection shown in FIG. 2.

The image detecting conditions in step S219 and step S214 have been described in the description of FIG. 2. However, if the beam current for taking the low-magnification image and the beam current for taking the high-magnification image, which are set herein, are configured to be set by the user through the computer terminal device 117, however, usability is improved. At this time, for example, a GUI (Graphical User Interface) as shown in FIG. 9 is made to be displayed in the computer terminal device 117, whereby the image detecting conditions are set. The item "probe current" in FIG. 9 corresponds to the beam current in the present specification. In addition to the probe current, "Field of View" representing the visual field of taking the image, the number of pixels per image, "image size" indicating, for example, 512×512 or 1024×1024, and "frame integration number" representing the number of times of scanning the beam with respect to the visual field, etc. can be set for each of the high magnification and the low magnification. Moreover, since an acceleration voltage cannot be rapidly varied in general, a common voltage is set herein for the low magnification and the high magnification.

Figure 3:
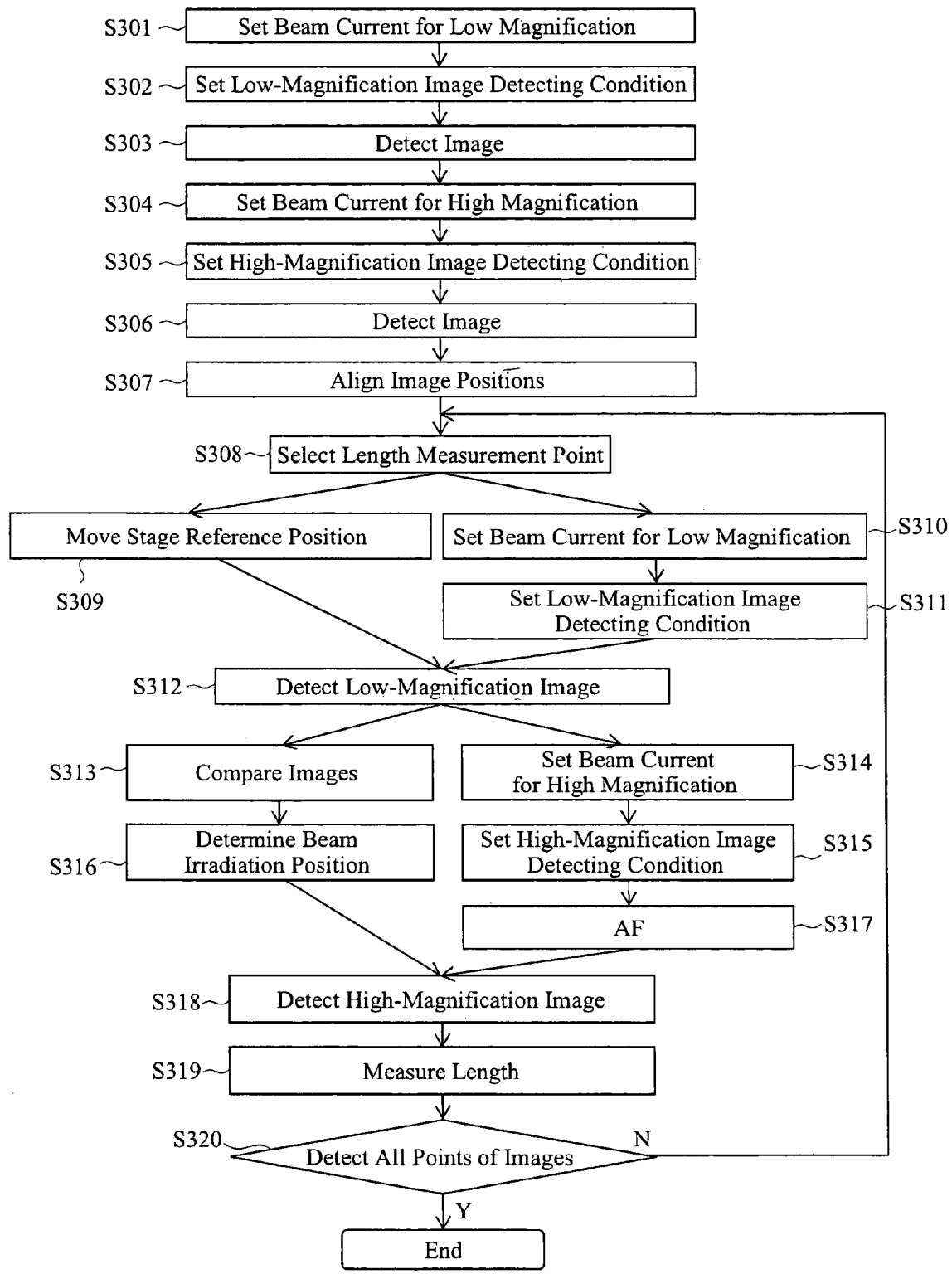
FIG. 3 is a flow chart showing a sequence of the case where length measurement of patterns is performed in the SEM according to the first embodiment of the present invention.

The sequence of the case where the electro-optical system of FIG. 1 is applied to an automatic defect image detection of the review SEM has been described in FIG. 2. However, a sequence of the case where the present function is applied to a length measurement SEM is shown in FIG. 3. FIG. 3 is a flow chart showing the sequence of the case where the SEM shown in FIG. 1 is applied to the length measurement SEM.

In FIG. 3, steps S301 to S307 are the same as the above-described steps S201 to S207 in FIG. 2 and so their descriptions will be omitted.

Positions to be subjected to length measurement are selected in step S308, and the XY stage 114 is moved in step S309, thereby causing length measurement points selected in step S308 to enter the visual field of the low-magnification image. At the same time, the beam current is switched in step S310, and setting of the electro-optical system for detecting the low-magnification image is performed in step S311. More specifically, the normal control amount of the electro-optical system for taking the low-magnification image is set, and the alignment of the axis of the beam current for taking the low-magnification image and the control amount for astigmatism correction, which have been saved in step S302, are set.

The image is taken in step S312. In step S313, the image taken in step S311 is compared to an image capable of specifying previously stored measurement points, whereby the image detecting point of the high-magnification image is specified. At the same time, the beam current is varied for taking the high-magnification image in step S314, and the electro-optical system for taking the high-magnification image is further set in step S315. More specifically, the normal control amount of the electro-optical system for taking the high-magnification image is set, and the alignment of the axis of the beam current for taking the high-magnification image and the control amount for astigmatism correction saved in step S305 are set.

Also, in step S316, based on the misalignment amount of the low-magnification image detection and the high-magnification image detection which are measured in step S307, the electron beam irradiation position where the measurement pattern is imaged at a center of the visual field when the electron beam is emitted.

The AF is performed in step S317, the high-magnification image is taken in step S318, and a portion in which the pattern is specified is measured from the high-magnification image taken in step S319.

Figure 10:
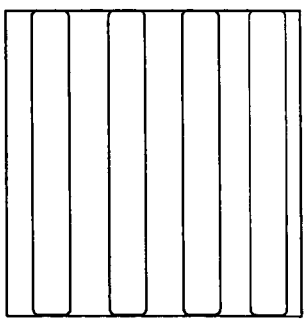
FIG. 10 is a view showing an example of a GUI for inputting image taken conditions in a sequence of pattern length measurement shown in FIG. 3.

FIG. 10 shows a GUI for setting the beam current and the image detecting conditions in the sequence of FIG. 3. In the length measurement SEM, since a portion to be measured is determined in advance, the low-magnification or high-magnification image can be confirmed so as to make a confirmation of whether an expected recipe can be confirmed. A method for setting image detecting conditions other than this is basically the same as that of FIG. 9.

Regarding a relation between the beam current and a spot diameter, chromatic aberration which is a main factor for determining the spot diameter is proportional to the beam current approximately to one-half power by an increase in an open angle of the beam involved in an increase in a beam current value although depending on the beam current. Therefore, in taking the high-magnification image, the beam current is suppressed small to reduce the spot diameter, whereby the high-resolution image is taken.

On the other hand, in the low-magnification image detection, when a fine defect is to be detected from a wide visual field or a position to be measured is to be accurately determined, the sampling number of images is increased from the general sampling number of 512×512 to, for example, 1024×1024 to perform sampling. In this case, when the beam current is increased by about four times to take the image, a decrease in the S/N due to a decrease in the signal amount per pixel is suppressed. When the beam current is increased by four times, the chromatic aberration is also increased by about two times. However, no problem is caused in the image quality as long as the accordingly enlarged spot diameter is smaller than the pixel size. When the low-magnification image is taken in the above-described manner, the frame integration number can be reduced and the image detecting time can be shortened.

Note that since the defect position has been already confirmed through the low-magnification image detection, taking the image in the wide visual field is not required at a time of the high-magnification image detection, so that taking the image thought the sampling of 512×512 preferably shortens the image detecting time.

A problem of shortening the image detecting time in the review SEM and the length measurement SEM is about the beam current switching time. Generally, the switching time takes several tens of seconds in order to switch the current by changing the extraction voltage of the FE electron gun, that is, becomes longer than the shortening of the image detecting time of the case where the beam current is increased. Therefore, instead of changing the extraction voltage of the FE electron gun, a method for changing the beam current by changing the aperture stop of the irradiation path of the electron beam will be described.

Figure 4:
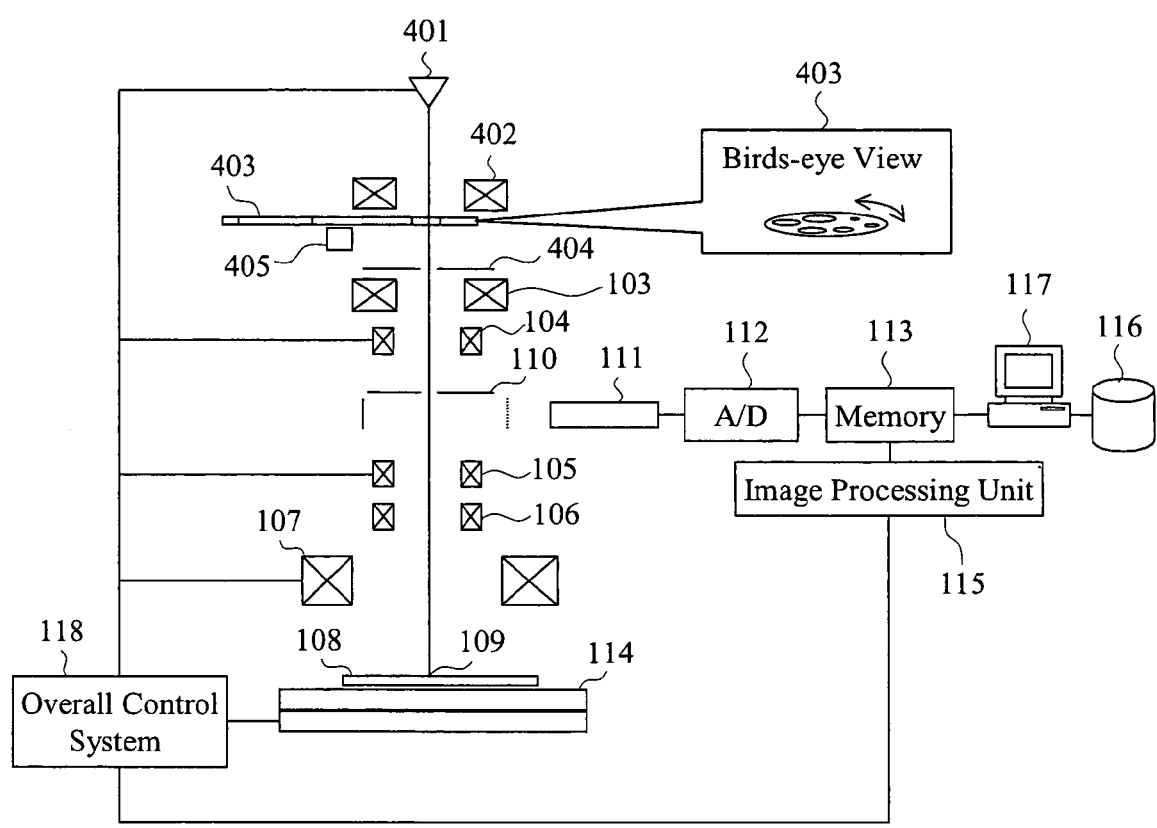
FIG. 4 is a view showing a configuration of an SEM according to another method of the present invention.

FIG. 4 is a view showing a configuration of an SEM according to the above method. When the SEM shown in FIG. 4 is compared with the above-described embodiment shown in FIG. 1, an aperture stop set 403, a field stop 404, and a stop changing means 405 are added and the electron beam source 101 is replaced by an electron beam source 401 and the condenser lens 102 is replaced by a condenser lens 402 and other configurations are the same as those of FIG. 1.

A plurality of stops having different diameters are provided in the aperture stop set 403, and the stop to be used can be selected by the stop changing means 405. When the small-diameter stop is used, the beam current becomes small. When the large-diameter stop is used, the beam current becomes large. When the image is to be taken at the low magnification, the large-diameter stop is used to increase the beam current. When the image is to be taken at the high magnification, the small-diameter stop is used to reduce the beam current. The position of the stop is mechanically changed by the stop changing means 405. However, the switching of the beam current within a range of 100 ms can be realized by virtue of employing the present method.

Figure 7:
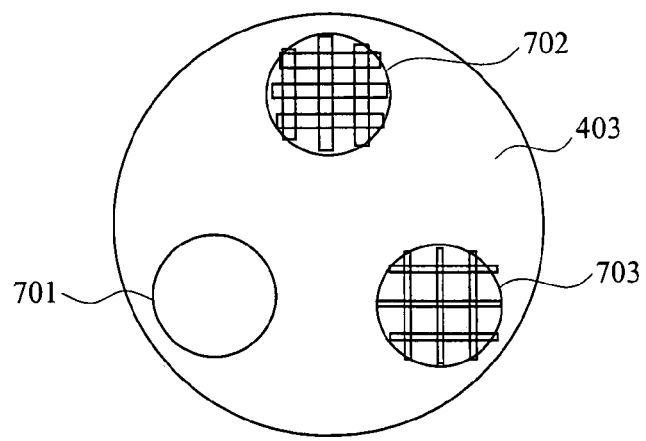
FIG. 7 is a view showing an example of a structure of an aperture stop set in the SEM shown in FIG. 4.

Note that although the stops are circular apertures with different diameters in the embodiment of FIG. 4, stops having shapes other than the shapes of apertures can be also employed. Such an example includes a mesh (net)-like stop shown in FIG. 7. For example, as shown in FIG. 7, an aperture stop 701 and mesh-like stops 702 and 703 are provided in the aperture stop set 403. The meshes provided in the aperture stop set 403 have different electron beam transmittance. When the mesh having high transmittance (for example, stop 703) is selected, the large beam current is set. When the mesh having low transmittance (for example, stop 702) is selected, the small beam current is obtained. Even when the transmittance is controlled by combining a plurality of apertures instead of the meshes, the same effects can be obtained.

In the embodiment of FIG. 4, an example for changing the beam current by mechanically changing the positions of the stops by the stop changing means 405 has been described. However, in this method, dust generated due to the mechanical movement in the case where the aperture stop set 403 is to be moved at a higher speed may be problematic. Thereat, an embodiment in which stops suitable for corresponding to the beam currents can be electrically selected is a SEM shown in FIG. 5.

Figure 5:
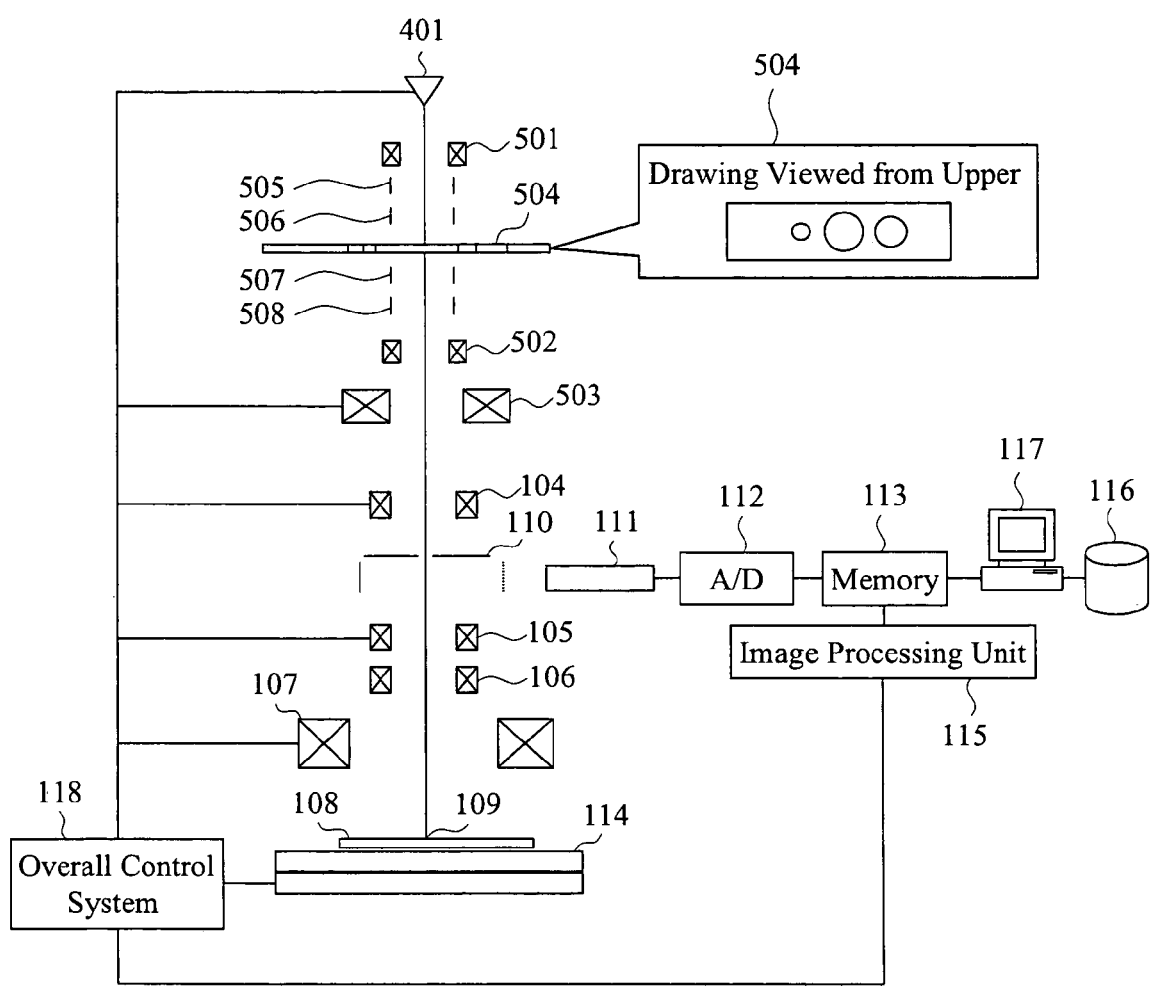
FIG. 5 is a view showing a configuration of an SEM according to another embodiment of the present invention.

When the SEM shown in FIG. 5 is compared with the above-described embodiment shown in FIG. 4, the condenser lenses 402 and 103, the aperture stop set 403, the field set 404, and the stop changing means 405 are replaced by first condenser lenses 501 and 502, a second condenser lens 503, an aperture stop set 504, and deflectors 505, 506, 507, and 508, and other configurations are the same as those of FIG. 4.

The electron beam generated by the electron beam source 401 is converged by the first condenser lenses comprised of a combination of the reference numerals "501" and "502", and is guided to the objective lens 107 through the second condenser lens 503. Stops with a plurality of apertures are formed in the aperture stop set 504. In the deflector 505, a voltage that causes the electron beam to be deflected so that the electron beam enters the stop which realizes the selected beam current is set. Then, a voltage is applied to the deflector 506 in an opposite direction so that the electron beam is incident in a direction orthogonal to the aperture stop set 504. Also, the deflector 507 and the deflector 508 causes the axis deflected for selecting the stop to return to the original axis of the electro-optical system in accordance with a method similar to that by the combination of the deflector 505 and the deflector 506. Other configurations are the same as those of the embodiment of FIG. 1, so that the description thereof will be omitted.

In the present method, the beam current can be changed merely by changing voltages of electrodes of the deflectors 505, 506, 507, and 508, so that no dust is generated and switching can be also performed at a high speed.

The embodiment of the case where the aperture stop set having the plurality of beam diameters is employed has been described above. However, providing the plurality of aperture stops is not required to control the amount of the beam passing through the stop. Such an embodiment is shown in FIG. 8.

Figure 8:
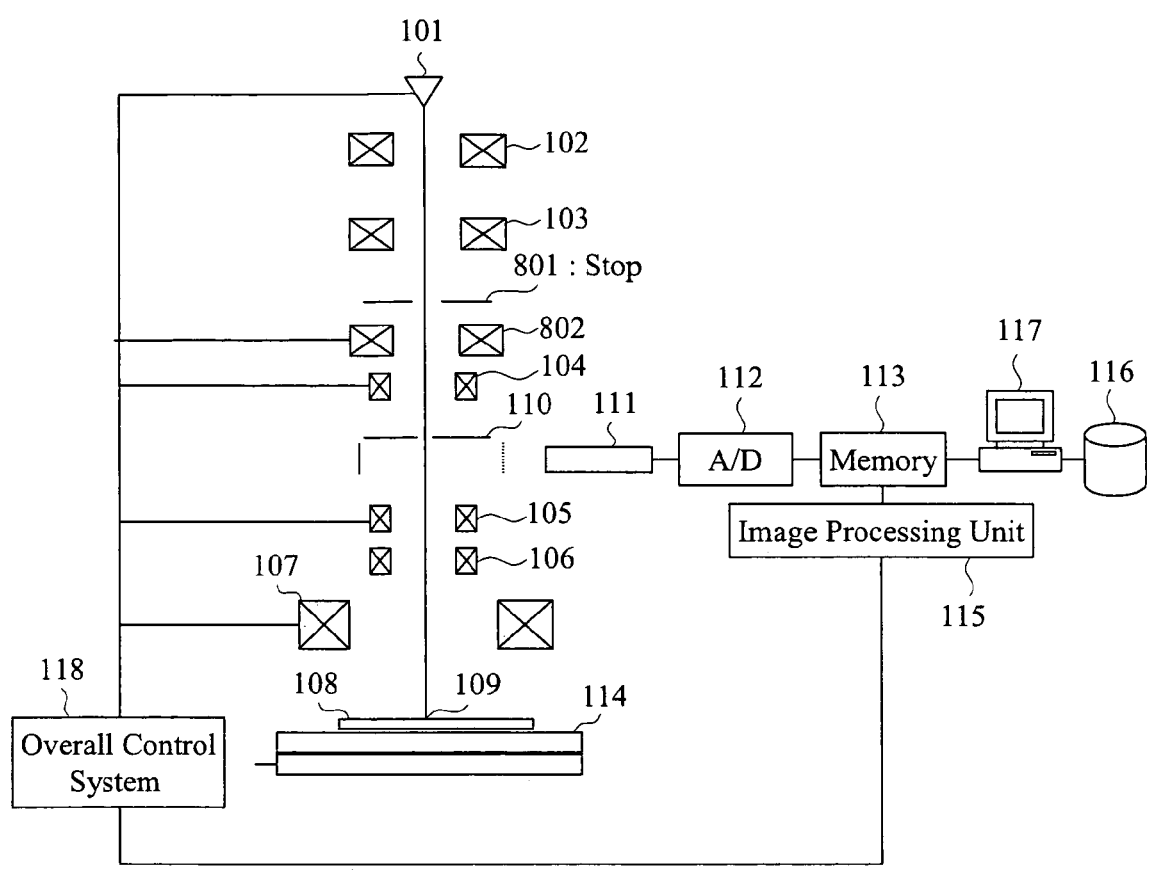
FIG. 8 is a view showing a configuration of an SEM according to another embodiment of the present invention.

In a SEM shown in FIG. 8, a stop 801 is disposed instead of the aperture stop set 403 in FIG. 4, and a condenser lens 802 is added. A stop amount of the beam at the position of the stop 801 can be adjusted by changing power of an electromagnetic lens of the condenser lens 103. When the beam width at the stop 801 is smaller than an aperture provided in the stop 801, the entire electron beam passes through the beam width. When the beam width is larger than the aperture, vignetting is caused and the beam current is suppressed to a low level. The position of the beam path varied in accordance with the power of the condenser lens 103 can be corrected by causing the condenser lens 802 to vary in combination with that.

A problem for realizing the SEMs shown in FIGS. 4, 5 and 8 is an occurrence of contamination (staining) in the stops. When the beam current is set low by the stops, the "vignetting" at the stops is considerably large compared with the conventional SEMs. Therefore, a gas present in a minute amount in vacuum may be burnt onto and attached to the stops due to an influence of the electron beam, and the quality of the image to be taken may possibly be changed along with time. A means for preventing this includes a method of increasing vacuum degree, and further includes another method of heating the aperture stop sets 403 and 504 so that no contaminant adheres to portions of the stops.

Incidentally, according to the above-described methods, an image having a high S/N can be obtained in the low-magnification image even if the beam current is large, but an image with a high S/N cannot be obtained in the high-magnification image if the beam current is not made small. However, this does not cause any big problem in practice.

For example, as for the automatic image detecting sequence of the defect images in the review SEM shown in FIG. 2, after the low-magnification images are taken in the step S212, the position of the defect has to be detected through comparison of the images in the step S213. On the other hand, after the high-magnification image of the defect is taken in the step S218, this image is stored in the secondary storage device 116 or the like and then an image of a defect to be the next target is taken. Thereafter, an image processing is performed, whereby the S/N of the high-magnification taken image is improved. In the low-magnification image, although an image processing for improving the S/N, which takes a calculation time, is difficult to be performed before the step S213 since the overall throughput are lowered. Meanwhile, as for the high-magnification image taken in the step S218, this can be implemented. Furthermore, the high-magnification image taken in the step S218 has the feature of readily performing a processing for improving the S/N.

Figure 6A:
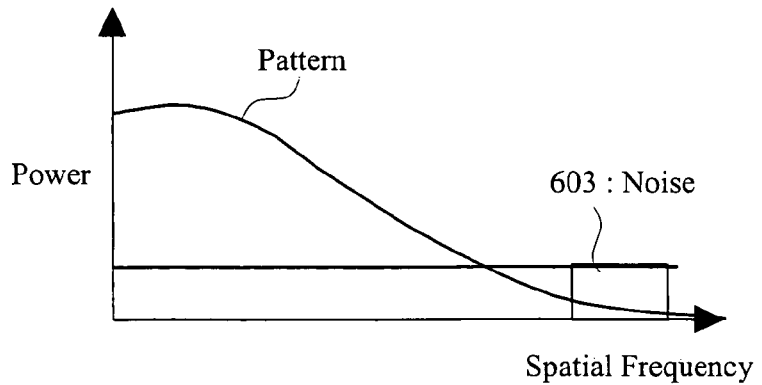
FIG. 6A is a view showing an energy distribution of spatial frequency in which pixel size of an entire low-magnification image is used as a reference.
Figure 6B:
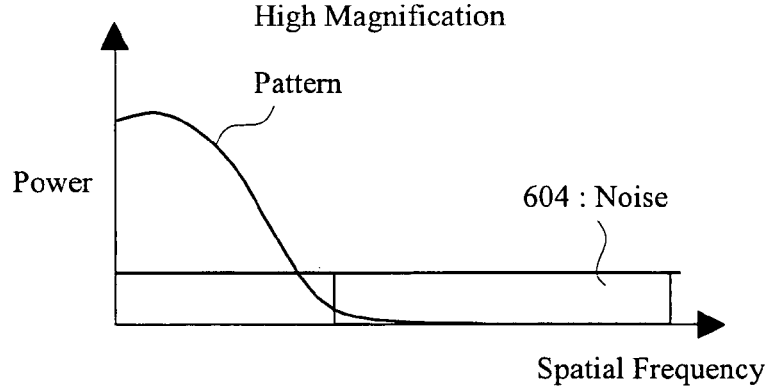
FIG. 6B is a view showing an energy distribution of spatial frequency in which pixel size in an entire high-magnification image is used as a reference.

This reason will be described with reference to FIGS. 6A and 6B. FIG. 6A shows an energy distribution of spatial frequency, in which pixel size in the entire low-magnification image is used as a reference. Meanwhile, FIG. 6B shows an energy distribution of spatial frequency which is the same as that in the high-magnification image.

Since the low-magnification image and the high-magnification image take the images with the same pattern, the energy image in the high-magnification image is offset to a band with the low spatial frequency as compared with the spatial frequency in which each pixel size is used as a reference. Meanwhile, the reference numerals "603" and "604" represent energy distributions of the spatial frequencies of noise. The noise shows a distribution generally called white noise and depending on no particular frequency. Therefore, in the high-magnification image in which the energy distribution of the spatial frequency is previously offset on a lower-frequency band, since components in a high-frequency band of the spatial frequency are suppressed, the S/N can be readily improved.

On the other hand, in the low-magnification image in which the large energy distribution is offset to a high-frequency band, such a processing is difficult to be performed.

Note that as a method for improving the S/N by utilizing a difference between the spatial-frequency distribution of noise and a spatial frequency distribution of the target, a method called "wavelet shrinkage" is known. Herein, an advantage of performing an S/N improving processing to the high-magnification image has been described in the sequence of automatic pickup of defect images. However, similarly thereto, since the S/N improving processing including a large calculation amount is performed only to the high-magnification image, the S/N improving processing can be readily performed also in the length measurement SEM. The reason that the S/N improving processing including the large calculation amount can be readily performed to the high-magnification image is as follows. That is, for example in the sequence of FIG. 2, in the case of taking the low-magnification image, immediately after the low-magnification image is taken in the step S212, specifying the defect position in the step S213 is required and therefore no spare time is left. However, in the case of taking the high-magnification image, after the high-magnification image is taken in the step S218, the stage has to be moved and therefore a spare time is present.

By using the above-described methods, even if the high-magnification image is taken in a state in which the beam current is small, the taken image can be converted into a good image. Therefore, the image detection can be performed in a state in which the frame addition is small, so that the image detecting time can be shortened.

Therefore, in the SEMs and the image detecting methods according to the present invention, the electron beam can be switched within a short time, and both the short-time low-magnification image detection and the high-resolution high-magnification image detection can be performed.

As described above, the invention made by the present inventors has been specifically explained based on the embodiments. However, needless to say, the present invention is not limited to the above-mentioned embodiments and may be variously altered and modified within a scope of not departing from the gist thereof.

For example, although the review SEM and the length measurement SEM have been described in the above-described embodiments, the present invention is not limited thereto and can be applied to other SEMs.

The present invention as described above can be applied to SEM semiconductor wafer inspection apparatuses, review SEMs, and length measurement SEMs, etc.

The invention may be embodied in other specific forms without departing from the spirit or essential characteristics thereof. The present embodiment is therefore to be considered in all respects as illustrative and not restrictive, and the scope of the invention being indicated by the appended claims rather than by the foregoing description and all changes which come within the meaning and range of equivalency of the claims are therefore intended to be embraced therein.

What is claimed is:

1. A scanning electron microscope comprising:
   an electron beam source for emitting an electron beam;
   an electron beam converging means for converging said electron beam on an observation target surface;
   a beam current control means for controlling a beam current of said electron beam;

an electron beam scanning means for making said electron beam being scanned on said observation target surface;

a scanning position correction means for controlling a scanning position of said electron beam scanning means;

an observation target moving means for moving said observation target so that said observation target surface is within a scanning range of said electron beam by said electron beam scanning means;

an electron detector for detecting a secondary electron or a reflected electron generated by scanning said electron beam on said observation target surface;

an image formation means for forming an image based on a detection value of said electron detector;

a signal gain adjusting means for adjusting a corresponding relation between the secondary electron or reflected electron detected by said electron detector and said image formation means;

a control amount memory means for saving in advance an adjustment amount of said signal gain adjusting means so that the detection value of said electron detector falls within a predetermined range in setting a plurality of beam currents or for saving a calculation algorithm of the adjustment amount; and an image detecting condition control means for changing an image detecting condition in accordance with a change in the beam current by using said adjustment amount or said calculation algorithm obtaining for the adjustment amount, which is saved in said control amount memory means.

2. The scanning electron microscope according to claim 1, wherein the beam current of said electron beam in said beam current control means is controlled by changing transmittance of said electron beam in an irradiation path of said electron beam.

3. The scanning electron microscope according to claim 2, wherein said beam current control means has an electron beam transmission device in which setting of the transmittance of said electron beam is different depending on a position, and an electron beam transmission device position changing unit for changing the setting position of said electron beam transmission device to change the transmittance of said electron beam.

4. The scanning electron microscope according to claim 2, wherein said beam current control means has an electron beam transmission device in which setting of the transmittance of said electron beam is different depending on a position, and an electron beam deflecting unit for controlling the transmittance of said electron beam by offsetting said electron beam to change a position where said electron beam passes through said electron beam transmission device.

5. The scanning electron microscope according to claim 3, wherein said electron beam transmission device has a heating unit for preventing contamination involved in transmission and shutoff of said electron beam.

6. The scanning electron microscope according to claim 1, wherein, further in said control amount memory means, a control amount of said scanning position correction means or a calculation algorithm of the control amount for realizing observation of a same part of said observation target surface in setting the plurality of beam currents is served.

7. An image detecting method of a scanning electron microscope, the method comprising:

a step of inputting coordinates of defects detected by an inspection apparatus for inspecting an observation target surface, selecting one of the coordinates of said defects, and moving said selected defect into an image detecting visual field of the scanning electron microscope;

a first image detecting step of making an electron beam converged into a spot-like shape scanning said observation target surface, and converting a secondary electron or reflected electron generated by the scan into an electrical signal to form an image;

a defect position specifying step of specifying a defect position on said observation target surface based on the image formed in said first image detecting step;

a second image detecting step of making an electron beam converged into a spot-like shape scanning the defect position specified in said defect position specifying step at a magnification larger than that used in said first image detecting step, and converting a secondary electron or reflected electron generated by the scan into an electrical signal to form an image;

a first beam current changing step of observing said observation target surface in the second image detecting step by using a beam current smaller than that used in said first image detecting step;

a first image detecting condition setting step of changing an image detecting condition to a condition previously set in taking an image at the beam current set in said first beam current changing step;

a second beam current changing step of setting a beam current employed in said first image detecting step; and a second image detecting condition setting step of setting the image detecting condition employed in said first image detecting step again, wherein said first beam current changing step and said first image detecting condition setting step are performed before said second image detecting step, and said second beam current changing step and said second image detecting condition setting step are performed after said second image detecting step.

8. The image detecting method of a scanning electron microscope according to claim 7, wherein the image detecting condition of said first image detecting condition setting step includes at least one of: a corresponding control amount with respect to said electron beam for suppressing, regardless of a change of the beam current by said first beam current changing step, brightness of the image generated in said second image detecting step so as to be brighter than brightness of the image generated in said first image detecting step; a corresponding relation control amount between the secondary electron or reflected electron generated in said scan for making said electron beam being converged in a spot-like shape on said observation target surface and brightness of an image to be formed; a scanning position correction amount for making said electron beam scanned at a portion specified on said observation target surface; and an electron beam convergence correction amount for making said electron beam being converged into a spot-like shape on said observation target surface.

9. The image detection method of a scanning electron microscope according to claim 7, further comprising an S/N increasing step of performing, to the image formed in said second image detecting step, a high S/N increasing image processing for improving a low S/N with respect to the image formed in said first image detecting step.

10. The image detection method of a scanning electron microscope according to claim 7,
  wherein, in said first beam current changing step and said second beam current changing step, a stop or an electron beam transmission device for controlling transmittance of said electron beam is inserted in an irradiation path of said electron beam so as to change said beam current.

11. The image detection method of a scanning electron microscope according to claim 7,
  wherein a sampling number of the image taken in said second image detecting step is larger than a sampling number of the image taken in said first image detecting step.

* * * * *